(12) United States Patent
Bonham et al.

(10) Patent No.: US 8,846,981 B2
(45) Date of Patent: Sep. 30, 2014

(54) 1,1-DI[(ALKYLPHENOXY)ETHOXY]CYCLO-HEXANES

(75) Inventors: James A. Bonham, Lake Elmo, MN (US); Stephan J. W. Platzer, Longmeadow, MA (US); Edward A. Casson, III, Wake Forest, NC (US)

(73) Assignee: Southern Lithoplate, Inc., Youngsville, NC (US)

( * ) Notice: Subject to any disclaimer, the term of this patent is extended or adjusted under 35 U.S.C. 154(b) by 431 days.

(21) Appl. No.: 13/361,129

(22) Filed: Jan. 30, 2012

(65) Prior Publication Data
US 2013/0197274 A1    Aug. 1, 2013

(51) Int. Cl.
*C07C 43/315*    (2006.01)
*C07C 41/48*    (2006.01)

(52) U.S. Cl.
CPC ............. *C07C 43/315* (2013.01); *C07C 41/48* (2013.01); *C07C 2101/14* (2013.01)
USPC ......................................... 568/593; 568/592

(58) Field of Classification Search
CPC .... C07C 41/48; C07C 43/315; C07C 2101/14
USPC .................................. 568/592, 593
See application file for complete search history.

(56) References Cited

U.S. PATENT DOCUMENTS

| | | | |
|---|---|---|---|
| 4,101,323 A | 7/1978 | Buhr et al. | 430/170 |
| 4,115,128 A | 9/1978 | Kita | 430/191 |
| 4,247,611 A | 1/1981 | Sander et al. | 430/286.1 |
| 4,356,252 A | 10/1982 | Lee | 430/270.1 |
| 4,619,998 A | 10/1986 | Buhr | 544/193.1 |
| 5,340,699 A | 8/1994 | Haley et al. | 430/302 |
| 5,399,778 A | 3/1995 | Steffen et al. | 568/591 |
| 5,480,762 A | 1/1996 | Toyama et al. | 430/302 |
| 5,731,123 A | 3/1998 | Kawamura et al. | 430/176 |
| 5,932,392 A | 8/1999 | Hirai et al. | 430/270.1 |
| 6,051,361 A | 4/2000 | Hattori et al. | 430/270.1 |
| 6,083,662 A | 7/2000 | Miller et al. | 430/302 |
| 6,165,676 A | 12/2000 | Hattori | 430/270.1 |
| 6,174,646 B1 | 1/2001 | Hirai et al. | 430/302 |
| 6,391,512 B1 | 5/2002 | Hirai et al. | 430/176 |
| 6,399,279 B1 | 6/2002 | Urano et al. | 430/302 |
| 7,147,995 B2 | 12/2006 | Takamiya | 430/331 |
| 7,229,739 B2 | 6/2007 | Perron et al. | 430/270.1 |
| 7,255,972 B2 | 8/2007 | Nishiwaki et al. | 430/270.1 |
| 7,332,259 B2 | 2/2008 | Takagi | 430/270.1 |
| 7,670,450 B2 | 3/2010 | Lamansky et al. | 156/235 |
| 7,682,776 B2 | 3/2010 | Teng | 430/302 |
| 2001/0009129 A1 | 7/2001 | Kunita et al. | 101/453 |
| 2006/0046187 A1 | 3/2006 | Kuroki et al. | 430/270.1 |
| 2006/0269869 A1 | 11/2006 | Takada | 430/270.1 |
| 2007/0065754 A1 | 3/2007 | Kuroki et al. | 430/270.1 |
| 2007/0172758 A1 | 7/2007 | Maehashi | 430/270.1 |
| 2007/0287097 A1 | 12/2007 | Suzuki et al. | 430/270.1 |
| 2009/0029283 A1 | 1/2009 | Takagi | 430/270.1 |
| 2009/0075201 A1 | 3/2009 | Miyoshi | 430/283.1 |
| 2009/0110832 A1 | 4/2009 | Sampei | 427/288 |
| 2009/0170139 A1 | 7/2009 | Mishima et al. | 435/11 |
| 2009/0311621 A1 | 12/2009 | Takagi | 430/270.1 |

FOREIGN PATENT DOCUMENTS

| | | |
|---|---|---|
| JP | 63-149640 | 6/1988 |
| JP | 09-171254 | 6/1997 |
| JP | 03-644002 | 4/2005 |

OTHER PUBLICATIONS

Thomas, Bejoy, et al. "Synthesis of Dimethyl Acetal of Keytones: Design of Solid Acid Catalysts for One-Pot Acetalization Reaction." Microporous and Mesoporous Materials 80 (2005) 65-72.
"Cyclohexanone." National Institute of Standards and Technology, Material Measurement Laboratory, 2011, data compilation Copyright by the U.S. Secretary of Commerce on behalf of the U.S.A. pp. 1-6.

*Primary Examiner* — Rosalynd Keys
(74) *Attorney, Agent, or Firm* — Roberts & Roberts, LLP

(57) ABSTRACT

Disclosed is a ketal having the formula:

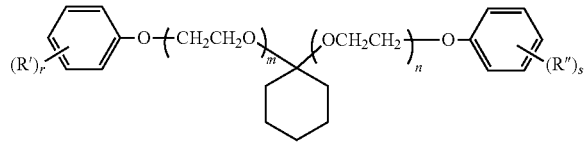

wherein R' and R'' independently are an alkyl group having from 8 to about 20 carbon atoms; m and n independently are an integer of from 1 to about 200; and r and s independently are an integer of from 1 to 3; and the method for preparing the ketal by transketalization using 1,1-dimethoxycyclohexane or 1,1-diethoxycyclohexane with an (alkoxyphenoxy)ethanol type of surfactant. The ketal is at least partially soluble in water.

22 Claims, No Drawings

1,1-DI[(ALKYLPHENOXY)ETHOXY]CYCLO-HEXANES

BACKGROUND OF THE INVENTION

1. Field of the Invention

The invention relates to ketal compounds that are useful as part of a coating composition for positive-working, lithographic printing plates, which are imagewise exposed to near-infrared radiation and then developed. More particularly, the invention relates to a particular class of ketals, namely, 1,1-di[(alkylphenoxy)ethoxy]cyclohexanes. These ketals comprise hydrophilic groups and lipophilic groups. In general, the ratio of the molecular mass of the hydrophilic groups relative to the molecular mass of the lipophilic groups determines the solubility of these ketals in different solvents. These ketals may be decomposed by acids to form surfactants, which can have solubility characteristics that are different than those of the starting ketal.

2. Description of the Related Art

It is known in the art that alcohols will react with the carbonyl group of aldehydes in the presence of an acid catalyst to yield acetals. These reactions are reversible. Therefore, the reaction is generally carried out by allowing the carbonyl group to react with an excess amount of the alcohol and by removing the water byproduct. Furthermore, it is also known in the art that alcohols are generally more difficult to react with the carbonyl group of ketones, in particular, cyclohexanone, to yield ketals, in this case, 1,1-dialkoxycyclohexane.

Simple 1,1-dialkoxycyclohexanes can be prepared by other methods, such as, by reacting a simple alcohol with cyclohexanone in the gas phase. This is described, using methanol, by K. B. Wiberg, K. M. Morgan, and H. Maltz in Thermochemistry of Carbonyl Reactions. 6. A study of hydration equibria, J. Am. Chem. Soc., 1994, 116, 11067-11077. Another method for making 1,1-dimethoxycyclohexane is by reacting methanol with cyclohexanone in the presence of a solid acid catalysts, as described by B. Thomas, S. Prathapan, and S. Sugunan in Synthesis of dimethyl acetal of ketones: design of solid acid catalysts for one-pot acetalization reaction, Microporous and Mesoporous Materials, 2005, 80, 65-72.

Other methods have been devised to produce simple 1,1-dialkoxycyclohexanes. For example, they can also be prepared by reacting cyclohexanone with a trialkoxymethane, such as trimethoxymethane, triethoxymethane, or triisopropoxymethane. For example, trimethoxymethane may be added to the carbonyl group of the cyclohexanone in the presence of an acid catalyst to yield the ketal and byproduct methyl formate. Such a reaction is described in U.S. Pat. No. 5,399,778.

Non-simple 1,1-dialkoxycyclohexanes are very difficult to make by reacting cyclohexanone with alcohols having long straight chains, branched chains, or aromatic groups. For example, 1,1-di(cyclohexyloxy)cyclohexane was made with a yield of 29% by reacting cyclohexanol with cyclohexanone, as described in U.S. Pat. No. 3,072,727. Non-simple 1,1-dialkoxycyclohexanes are typically made by transketalization, namely, by mixing and heating such alcohols with an already formed simple 1,1-dialkyoxycyclohexane, namely, with methoxy, ethoxy, or isopropoxy groups. For example, 2-phenoxyethanol can be mixed with 1,1-dimethoxycyclohexane to form 1,1-di(2-phenoxyethoxy)cyclohexane. This reaction is described in U.S. Pat. No. 6,165,676 and U.S. Pat. No. 6,391,512.

There is great commercial interest in lithographic printing plates having coatings that are digitally imageable using near-infrared laser exposure. With positive-acting plates, once the coating is imagewise exposed to infrared radiation, the exposed areas are easily removed, while the unexposed areas remain as the image. Positive-working, imageable compositions containing novolak or other phenolic polymeric binders and diazoquinone imaging components have been prevalent in the lithographic printing plate and photoresist industries for many years. Imageable compositions based on alkali-soluble phenolic resins with various dissolution inhibitors and infrared radiation absorbing compounds are also well known. The dissolution inhibitors are believed to prevent dissolution by hydrogen bonding of the normally alkali-soluble phenolic resins prior to imaging. During actinic exposure, it is generally believed that the mechanism of image formation occurs by an increase in alkaline solubility due to a disruption or breaking of the hydrogen bonds.

The use of dissolution inhibitor compounds having acid-cleavable C—O—C groups in positive-working printing plates is also well known. Representative of such compounds are 2-tetrahydropyranyl ethers described in U.S. Pat. No. 3,779,778; ortho-carboxylic acid esters described in U.S. Pat. No. 4,101,323; polyacetals described in U.S. Pat. No. 4,247,611; and ketals described in U.S. Pat. No. 6,165,676. These compounds prevent dissolution of normally alkali-soluble phenolic resins in alkaline developer solutions.

Moreover, these dissolution inhibitors are generally mixed with photolytic acid-generating compounds in the photosensitive layers of the printing plates. Upon imagewise exposure of the layers to actinic radiation, an acid is released from the photolytic acid-generating compound that then catalyzes the decomposition of the dissolution inhibitors in the exposed regions. When this occurs, the exposed region can then be selectively dissolved in an aqueous-based, alkaline developer.

Simple ketals of 1,1-dialkoxycyclohexane are generally poor dissolution inhibitors, due to the lack of hydrogen bonding sites. Examples of simple ketals include 1,1-dimethoxycyclohexane (Mw 144), 1,1-diethoxycyclohexane (Mw 172), and 1-1-di(1-methoxyethoxy)cyclohexane (Mw 200).

A particular class of ketal dissolution inhibitors of the class 1,1-di[(alkylphenoxy)ethoxy]cyclohexanes having the general formula

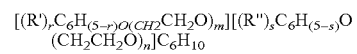

wherein m and n independently are an integer of from 1 to 5; r and s independently are an integer of from 1 to 3; and R' and R" independently are a hydrogen atom or an alkyl group having 1 to 5 carbon atoms are described in U.S. Pat. No. 6,165,676; U.S. Pat. No. 6,391,512; U.S. Pub. No. 2007/0172758; and U.S. Pub. No. 2009/0075201. The alkyl groups of R' and R" may be straight or branched, and include methyl, ethyl, propyl, butyl, and pentyl groups. The specific example of such ketals in the above-mentioned patents and patent applications is the ketal wherein m and n are 1; and R' and R" are hydrogen atoms. The formula for this specific ketal is $[C_6H_5O(CH_2CH_2O)][C_6H_5O(CH_2CH_2O)]C_6H_{10}$. This 1,1-di(2-phenoxyethoxy)cyclohexane is water insoluble. Strong acids will decompose this ketal into cyclohexanone and 2-phenoxyethanol, which has a low solubility of 27 g/l in water. It is desired that the compounds in the photosensitive layer after exposure to near-infrared light be soluble in an aqueous developer. Due to their water-insoluble characteristics, neither this specific ketal nor its acid-decomposed part is suitable for an aqueous developer. Furthermore, due to the relatively low molecular weight of 356 for this specific ketal, lithographic coatings with this ketal tend to have lower printing durability in the image areas of the printing plate. In addition, due to the lack of lipophilic alkyl groups on this specific ketal, coatings with this ketal tend to not accept printing inks well.

SUMMARY OF THE INVENTION

The invention provides a ketal having the Formula 1:

Formula 1

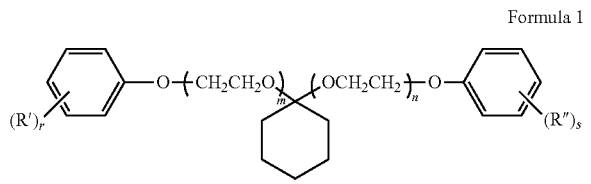

wherein R' and R" independently are an alkyl group having from 8 to about 20 carbon atoms;
m and n independently are an integer of from 1 to about 200; and
r and s independently are an integer of from 1 to 3.

The invention further provides a method of preparing a ketal having the Formula 1, wherein R' and R" independently are an alkyl group having from 8 to about 20 carbon atoms; m and n independently are an integer of from 1 to about 200; and r and s independently are an integer of from 1 to 3; the method comprising reacting a 1,1-dimethoxycyclohexane or 1,1-diethoxycyclohexane with an (alkylphenoxy)ethanol type of alcohol whose alkyl group has from 8 to about 20 carbon atoms; in the presence of an acid catalyst and an optional organic solvent at a temperature from about 60° C. to about 180° C., to produce a result; then removing the produced methanol from 1,1-dimethoxycyclohexane or the produced ethanol from 1,1-diethoxycyclohexane to produce a modified result; then optionally treating the modified result with an aqueous base until a pH of from about 6 to about 7 is attained, and then recovering the resulting ketal by separating it from the aqueous phase.

DESCRIPTION OF THE INVENTION

The present invention provides an acid decomposable 1,1-di(alkylphenoxyethoxy)cyclohexane which is partially or totally soluble in water, has both hydrophilic groups and lipophilic groups, and has a boiling point of about 200° C. or higher. The 1,1-di(alkylphenoxyethoxy)cyclohexanes may be prepared by a transketalization reaction of 1,1-dimethoxycyclohexane or 1,1-diethoxycyclohexane with (alkylphenoxy)ethanols. Surprisingly, the ketal compounds of the invention are partially or totally water-soluble and can be prepared from surfactants that are water-insoluble. The ketals may be converted back to the starting water-insoluble surfactants by acid decomposition. The ketal compounds of the invention are stable and do not evaporate in coatings during the drying process at a temperature of above 80° C. These ketal compounds are especially useful as dissolution inhibitors used in compositions for positive-acting, lithographic plates imaged with thermal energy, namely, near-infrared light. These compositions with ketal compounds of the present invention exhibit better development characteristics and improved press performance, while maintaining good shelf life.

The inventive ketals have the Formula 1, wherein R' and R" independently are an alkyl group having from 8 to about 20 carbon atoms; m and n independently are an integer of from 1 to about 200; and r and s independently are an integer of from 1 to 3.

In one embodiment of the invention wherein R' and R" independently are an alkyl group having from 8 to about 12 carbon atoms. In another embodiment, R' and R" are the same alkyl group. In one embodiment, R' and R" independently are a straight-chain alkyl group, while in another embodiment R' and R" independently are a branched-chain alkyl group. Non-limiting representative examples of R' and R" as straight chain alkyl groups include 1-octyl; 2-octyl; 3-octyl; 4-octyl; 1-nonyl; 2-nonyl; 5-nonyl; 1-decyl; 2-decyl; 1-undecyl; 2-undecyl; 1-dodecyl; 2-dodecyl; 1-tridecyl; 1-tetradecyl; 2-tetradecyl; 1-pentadecyl; 1-hexadecyl; 2-hexadecyl; 1-heptadecyl; 1-octadecyl; 1-nonadecyl; and 1-eicosyl. Non-limiting examples of R' and R" as branched-chain alkyl groups include 1,1,3,3-tetramethyl-1-butyl; 3-ethyl-2,2-dimethyl-3-pentyl; 2-propyl-1-pentyl; 1,1,4,4-tetramethyl-1-pentyl; 2,4,4-trimethyl-1-pentyl; 5,5-dimethyl-1-hexyl; 2-ethyl-1-hexyl; 3,5,5-trimethyl-1-hexyl; 2,6-dimethyl-4-heptyl; 3,6-dimethyl-3-heptyl; 4-methyl-3-heptyl; 6-methyl-2-heptyl; 2-butyl-1-octyl; 3,7-dimethyl-1-octyl; 3,7-dimethyl-3-octyl; 3-methyl-3-octyl; 2-hexyl-1-decyl; and 2-octyl-1-dodecyl. In one embodiment, R' and R" independently are 1,1,3,3-tetramethyl-1-butyl or 1,1,4,4-tetramethyl-1-pentyl.

In one embodiment of the invention, r and s of Formula 1 are the same integer, and most preferably are the integer I. In another embodiment of the invention, R' and R" are each attached at the 4 position of their respective phenyl group.

The numbers m and n of Formula 1 represent the average number of ethoxy groups per alkylphenoxy unit. In an embodiment of the invention, m and n of Formula 1 independently are more preferably an integer of from 1 to about 100; and most preferably an integer of from 1 to about 30. In another embodiment of the invention, m and n are the same integer.

The ketal compounds of the present invention represented by Formula 1 are prepared by an acid catalyzed transketalization reaction of 1,1-dimethoxycyclohexane or 1,1-diethoxycyclohexane with alcohols having a phenoxy group, at least one ethoxy group, and at least one alkyl group, wherein the phenoxy group is between the ethoxy group(s) and the alkyl group(s). These alcohols are selected from surfactants such as (alkylphenoxy)ethanol surfactants. The preferred alcohols are selected from the group of 2-(alkylphenoxy)ethanol surfactants or from the group of 2[2-(alkylphenoxy)polyethoxy]ethanol surfactants. The reaction is illustrated in the general Equation 1, wherein R is either a methyl group or an ethyl group. The other symbols, namely, R', R", m, n, r, and s, are defined above for Formula 1.

Equation 1

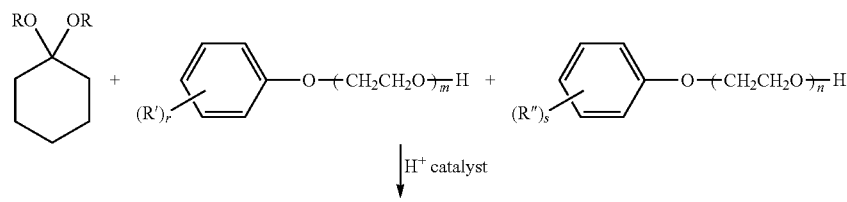

-continued

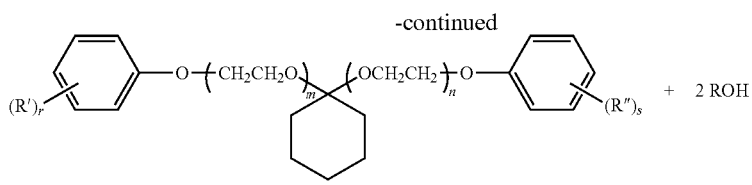 + 2 ROH

The reaction is conducted in the presence of an acid catalyst. Useful acid catalysts non-exclusively include Lowry-Bronsted acids which give up a proton. Non-exclusive examples of carboxylic acids, which are Lowry-Bronsted acids, include formic acid, acetic acid, oxalic acid, benzoic acid, and p-toluic acid. Preferred Lowry-Bronsted acids include phosphonic acids and sulfonic acids. Most preferred Lowry-Bronsted acids are sulfonic acids. Useful sulfonic acids include benzenesulfonic acid, p-toluenesulfonic acid (also known as 4-methylbenzenesulfonic acid), and 2-naphthalene sulfonic acid.

The reaction is optionally conducted with the components in admixture with an organic solvent. Useful organic solvents non-exclusively include cyclohexane, benzene, and toluene. A preferred solvent includes toluene.

The reaction is usually conducted at a temperature from about 60° C. to about 180° C., preferably from about 80° C. to about 120° C. to produce a result. The reaction solution is allowed to reflux and the low molecular weight alcohol byproduct is removed by azeotropic distillation. Methanol is removed when 1,1-dimethoxycyclohexane is used, or ethanol is removed when 1,1-diethoxycylcohexane is used. The reaction progress can be followed by the decrease in the FTIR absorption peak between 3200 $cm^-$ and 3500 $cm^-$, which corresponds to the O—H stretch of the alcohol. Upon completion of the reaction, it is preferred to neutralize the result by treating it with an aqueous base until a pH of from about 6 to about 7 is attained. This neutralization step increases the stability of the ketal. A suitable aqueous base includes a water solution of sodium hydroxide or potassium hydroxide. The reaction solution is dried over anhydrous potassium carbonate, filtered, and then concentrated under a reduced pressure. The purity of the resulting ketal, as determined by HPLC, is greater than 95%.

The hydroxyl compounds that are preferred for this invention are selected from the derivatives of polyoxyethylene compounds, and, of these compounds, the most preferred are those considered to be surface-active condensation products of polyoxyethylene. A thorough description of these compounds can be found in Nonionic Surfactants, 1967, Vol. 1, Chapters 1-12; Cationic Surfactants Organic Chemistry, 1990, Vol. 34, Chapters 1-2; and Alkylene Oxides and Their Polymers, 1990, Vol. 35, Surfactant Science Series, Marcel Dekker, Inc. (New York, N.Y.). Many of these compounds are commercially available and are described in McCutcheons 2009, Volume 1: Emulsifiers & Detergents, and Volume 2: Functional Materials, Manufacturing Confectioner Publishing Company (Princeton, Wis.).

Non-limiting representative examples of the (alkylphenoxy)ethanol type of alcohols useful in the preparation of the ketals of the present invention are listed in Table 1.

TABLE 1

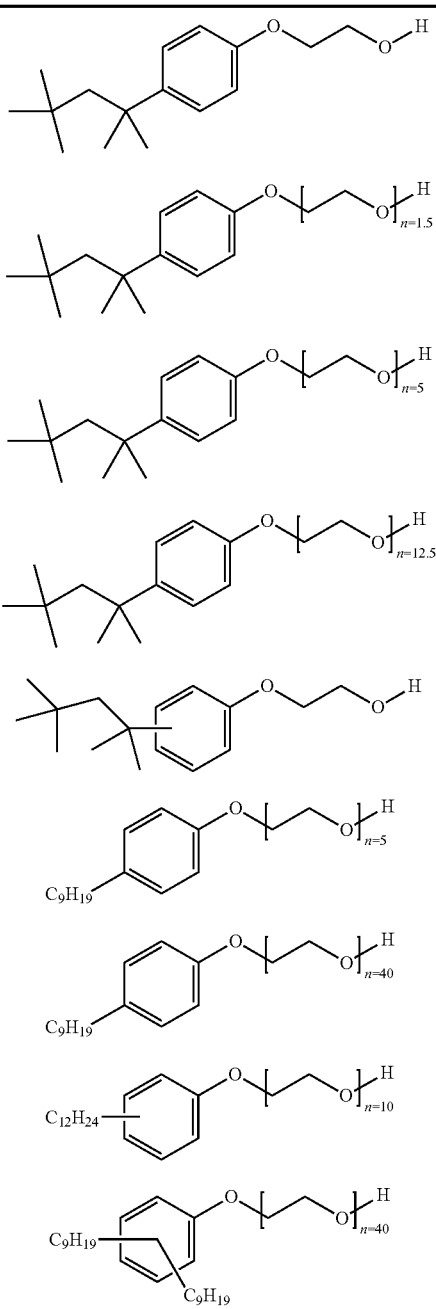

Preferred (alkylphenoxy)ethanols whose alkyl group has from 8 to about 20 carbon atoms non-exclusively include 2-[2-(octylphenoxy)polyethoxy]ethanol (CAS 9036-19-5), such as those from the Igepal CA series; 2-[2-(4-octylphenoxy)polyethoxy]ethanol (CAS 9002-93-1), such as those from the Triton X series; 2-[2-(nonylphenoxy)polyethoxy]

ethanol (CAS 9016-45-9), such as those from the Igepal CO series; 2-[2-(4-nonylphenoxy)polyethoxy]ethanol (CAS 127087-87-0), such as those from the Tergitol NP series; 2-[2-(isononylphenoxy)polyethoxy]ethanol (CAS 37205-87-1), such as those from the Neonal AF series; 2-[2-branchednonylphenoxy)polyethoxy]ethanol (CAS 68412-54-4); 2-[2-(dodecylphenoxy)polyethoxy]ethanol (CAS 9014-92-0), such as those from the Igepal RC series; and 2-[2-(dinonylphenoxy)polyethoxy]ethanol (CAS 9014-93-1), such as those from the Igepal DM series. The most preferred (alkylphenoxy)ethanols whose alkyl group has from 8 to about 10 carbon atoms nonexclusively include 2-[4-(1,1,3,3-tetramethylbutyl)phenoxy]ethanol, such as Triton X-15; 2-{2-[(1,1,3,3-tetramethylbutyl)phenoxy]polyethoxy}ethanol with four ethoxy groups, such as Igepal CA-520; 2-{2-[4-(1,1,3,3-tetramethylbutyl)phenoxy]polyethoxy}ethanol with nine ethoxy groups, such as Triton X-100; and 2-{2-[4-(1,1,3,3-tetramethylbutyl)phenoxy]polyethoxy}ethanol with twenty nine ethoxy groups, such as Triton X-305, but without the 30% water. Some commercially available (alkylphenoxy)ethanols are listed in U.S. Pub. No. 2009/0170139. It is well known that the average number of ethoxy groups in these surfactants usually is determined by the mole ratio of ethylene oxide to the alkylphenol used in making these surfactants. Analysis by mass spectrometry or nuclear magnetic resonance, for example, shows that when the average mole ratio is equal to 5, then the individual mole ratios may range from 2 to 8. For example, see U.S. Pat. No. 5,484,919, page 23, line 1, for an analysis of Igepal CO-520.

In another embodiment, it is advantageous that the ketals of the present invention can be prepared from a wide range of 2-[2-(alkylphenoxy)polyethoxy]ethanol surfactants. These surfactants are amphiphilic, containing both a hydrophilic part and a lipophilic part, namely, the ethoxy moiety and the alkylphenoxy moiety, respectively. It is reasonable to expect that the nature of the hydrophilic part and the lipophilic part of the surfactants will greatly influence the properties of the ketals of the invention. Each alkylphenoxy moiety at the ends of the ketal molecule can be selected to have a particular carbon chain-length alkyl fragment, having eight or greater number of carbons, up to 20, while each ethoxy moiety in the middle of the ketal molecule can be selected to have a particular number of ethoxy groups, from 1 to about 200. The cyclohexane moiety at the center of the ketal molecule will influence to some degree the amphiphilic nature of the ketal molecule. However, the nature of the lipophilic alkyl substituents on the two alkylphenoxy moieties and the number of hydrophilic ethoxy groups would be expected to greatly influence the ketal's amphiphilic properties and its behavior in a liquid solution and in a dry coating. This especially applies to optimizing the performance of these ketals as dissolution inhibitors in coatings useful in thermal-sensitive, positive-working, lithographic coatings. This includes the important properties of hydrogen bonding, solubility in coating solvents and processing chemicals, ink/water balance, and press life.

The ketal compounds of the invention represented by Formula 1 were surprisingly discovered to be partially or totally soluble in water even when prepared from surfactants that are water-insoluble. Likewise, these ketals were found to be partially or completely soluble in the aqueous alkaline developers commonly used to develop positive-working coatings. These ketals have a boiling point of about 200° C. or higher. The higher boiling point minimizes their evaporation from coatings, especially during the drying process of removing coating solvents, which require a high drying temperature, generally above about 80° C.

The compounds of this invention are improved dissolution inhibitors in the well-known positive-acting, lithographic compositions containing phenolic binders.

The physical properties of the ketals of the present invention are believed responsible for the improved performance. For example, these ketals are medium-to-high viscosity liquids or waxy solids. It is expected that these ketals remain in that state in the coating composition. It is postulated that their physical state enhances their ability to act as dissolution inhibitors by the formation of hydrogen bonds in the liquid state during the drying of the coating at above about 80° C. and then during the cooling of the coating to room temperature. The disruption of the hydrogen bonds and possibly of other bonds caused by the much higher temperatures achieved in the thermal heating in the imaged area will enhance solubility, leading to greater solubility difference between the exposed and nonexposed areas. Ketals that have lower chain alkyl groups attached to the phenoxy group and lower number of ethoxy groups, such as those described in U.S. Pat. No. 6,165,676, are crystalline. It is postulated that these crystalline ketals form crystals slowly in the coatings, leading to a non-uniform distribution of the ketals. Furthermore, these ketals and their resulting alcohols are water-insoluble, whereas the ketals of the present invention are either partially or completely water-soluble which is believed to be responsible for easier removal of the thermally exposed regions by the processing fluid, which is most commonly an aqueous alkaline solution.

EXAMPLES

Example 1

The following preparation illustrates the preparation of a ketal of Formula 1 wherein R' and R" each are a branched-chain alkyl group having 8 carbon atoms, and wherein m and n each are the integer 1, giving one ethoxy group on each side.

A stirred mixture of 72 g (0.5 mol) of 1,1-dimethoxycyclohexane, 250 g (1.0 mol) of 2-[4-(1,1,3,3-tetramethylbutyl)phenoxy]ethanol, 0.080 g of p-toluenesulfonic acid, and 300 ml of toluene was reacted in a flask with a thermometer and fractional distillation column at 120° C. for 8 hours with continuous stirring. The low boiling methanol that was produced during the reaction was removed. The reaction mixture was cooled to room temperature and washed with a small amount of an aqueous 1.0 M sodium hydroxide solution until the mixture was neutralized. The reaction mixture was then washed with a saturated sodium chloride solution to remove any remaining water in the toluene. Next the reaction mixture was dried over anhydrous potassium carbonate to remove any minor amounts of water and to make sure all of the p-toluenesulfonic acid was removed. The resulting mixture was filtered. The filtrate was evaporated under reduced pressure at 60° C. until all of the toluene was removed. A high viscosity, clear liquid was obtained upon cooling to room temperature, and is partially soluble in water. This ketal can be converted back to the starting surfactant and cyclohexanone by the addition of an acid, such as p-toluenesulfonic acid. The starting surfactant is water-insoluble. This ketal with a theoretical molecular weight of 580 has the structural formula shown below.

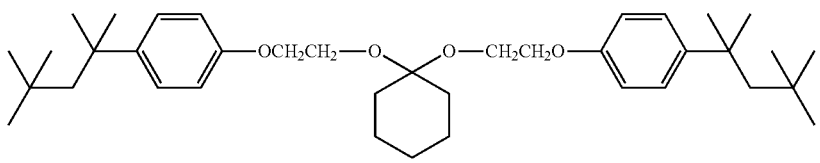

Example 2

The following preparation illustrates the preparation of a ketal of Formula 1 wherein R' and R" each are a branched-chain alkyl group having 8 carbon atoms, and wherein m and n each are the integer 5, giving an average of 5 ethoxy groups on each side.

The procedure as described in Example 1 was repeated but with 426 g (1.0 mol) of Igepal CA-520 instead of 250 g (1.0 mol) of 2-[4-(1,1,3,3-tetramethylbutyl)phenoxy]ethanol. Igepal CA-520, is a 2-{2-[4-(1,1,3,3-tetramethylbutyl)phenoxy]polyethoxy}ethanol, commercially available from Rhodia where the average number of ethoxy groups in the polyethoxy chain is 4. A medium viscosity, clear liquid was obtained upon cooling to room temperature, and is partially soluble in water. This ketal with a theoretical molecular weight of 932 has the structural formula shown below.

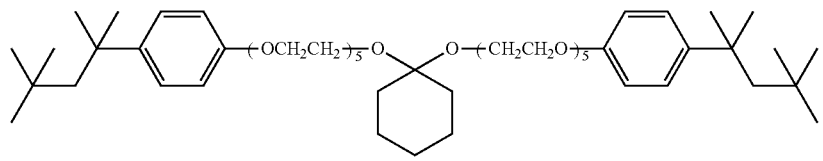

Example 3

The following preparation illustrates the preparation of a ketal of Formula 1 wherein R' and R" each are a branched-chain alkyl group having 8 carbon atoms, and wherein m and n each are the integer 10, giving an average of 10 ethoxy groups on each side.

The procedure as described in Example 1 was repeated but with 646 g (1.0 mol) of Triton X-100 instead of 250 g (1.0 mol) of 2-[4-(1,1,3,3-tetramethylbutyl)phenoxy]ethanol. Triton X-100 is 2-{2-[4-(1,1,3,3-tetramethyl butyl)phenoxy]polyethoxy)ethanol commercially available from Dow Chemical where the average number of ethoxy groups in the polyethoxy chain is 9. A medium viscosity, clear liquid was obtained upon cooling to room temperature, and is partially soluble in water. This ketal with a theoretical molecular weight of 1372 has the structural formula shown below.

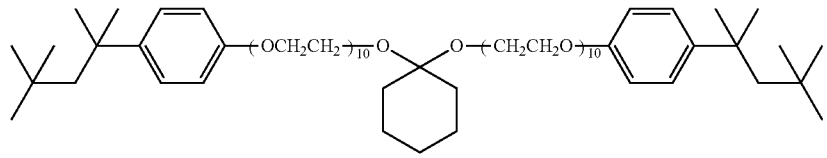

Example 4

The following preparation illustrates the preparation of a ketal of Formula 1 wherein R' and R" each are a branched-chain alkyl group having 8 carbon atoms, and wherein m and n each are the integer of 30, giving an average of 30 ethoxy groups on each side.

Triton X-305 is commercially available from Dow Chemical as a 70% solid in water. The solution was heated to 85° C. to remove the water. The resulting solid is 2-{2-[4-(1,1,3,3-tetramethylbutyl)phenoxy]polyethoxy}ethanol where the average number of ethoxy groups in the polyethoxy chain is 29. This solid is readily soluble in toluene. The procedure as described in Example 1 was repeated using 1526 g (1.0 mol) of this solid instead of 250 g (1.0 mol) of 2-[4-(1,1,3,3-tetramethylbutyl)phenoxy]ethanol. A waxy solid (m.p. 42° C.) was obtained upon cooling to room temperature, and is soluble in water. This ketal with a theoretical molecular weight of 3132 has the structural formula shown below.

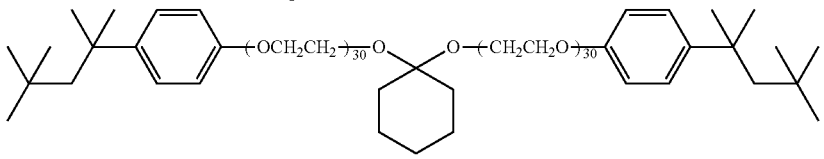

Comparative Example A

The following preparation illustrates the preparation of a ketal (CAS 115815-82-2) of Formula 1 wherein R' and R" do not exist, and wherein m and n each are the integer 1, giving one ethoxy group on each side. The ketal is made from 2-phenoxyethanol.

The procedure as described in Example 1 was repeated but with 138 g (1.0 mol) of 2-phenoxyethanol instead of 250 g (1.0 mol) of 2-[4-(1,1,3,3-tetramethylbutyl)phenoxy]ethanol. A white crystalline material (m.p. 50° C.) formed after sitting for a week in an open container at room temperature. When the crystalline material was heated to 85° C. and then cooled to room temperature, the formed liquid would again take more than a day to recrystallize at room temperature. This ketal is water-insoluble. It can be converted back to the starting alcohol and cyclohexanone by the addition of an acid, such as p-toluenesulfonic acid. The starting alcohol 2-phenoxyethanol has low water solubility. This comparative example ketal with a molecular weight of 356 has the structural formula shown below.

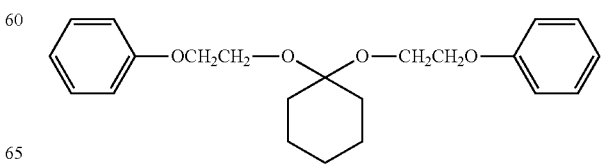

Comparative Example B

The following preparation illustrates the preparation of a ketal of Formula 1 wherein R' and R" each are a branched-chain alkyl group having 4 carbon atoms, and wherein m and n each are the integer 1, giving one ethoxy group on each side. The ketal is made from 2-[4-(1,1-dimethylethyl)phenoxy]ethanol.

The procedure as described in Example 1 was repeated but with 194 g (1.0 mol) of 2-[4-(1,1-dimethylethyl)phenoxy]ethanol instead of 250 g (1.0 mol) of 2-[4-(1,1,3,3-tetramethylbutyl)phenoxy]ethanol. A white crystalline material (m.p. 46° C.) formed after one day in an open container at room temperature. When the crystalline material was heated to 85° C. and then cooled to room temperature, the formed liquid would again take more than a day to recrystallize at room temperature. This ketal is water-insoluble. It can be converted back to the starting alcohol and cyclohexanone by the addition of an acid, such as p-toluenesulfonic acid. The starting alcohol 2-[4-(1,1-dimethylethyl)phenoxy]ethanol is also water-insoluble. This comparative ketal with a molecular weight of 468 has the structural formula shown below.

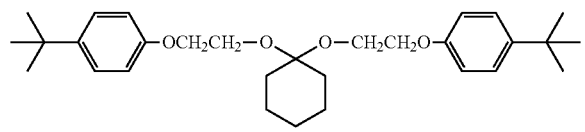

Comparison Table

The physical appearance of the ketals from Examples 1-4 and from Comparative Examples A-B are given in the following table, along with their solubility in deionized water and in a 1.0 M NaOH water solution. A typical aqueous alkaline developer for a positive-working, lithographic printing plate contains roughly 5% by weight of NaOH or KOH. A 1.0 M NaOH solution is equivalent to 4% by weight of NaOH.

| Ketal of Invention | Mw | Carbons in R'R" | Values m n | Physical Appearance | Solubility in DI Water | Solubility in 1.0M NaOH |
|---|---|---|---|---|---|---|
| Example 1 | 580 | 8 8 | 1 1 | high viscosity liq. | partially | partially |
| Example 2 | 932 | 8 8 | 5 5 | med. viscosity liq. | partially | partially |
| Example 3 | 1372 | 8 8 | 10 10 | med. viscosity liq. | partially | partially |
| Example 4 | 3132 | 8 8 | 30 30 | waxy solid | soluble | soluble |
| Comp. Ex. A | 356 | 0 0 | 1 1 | crystalline solid | insoluble | insoluble |
| Comp. Ex. B | 468 | 4 4 | 1 1 | crystalline solid | insoluble | insoluble |

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives that have been discussed above, and all equivalents thereto.

What is claimed is:

1. A ketal having the formula:

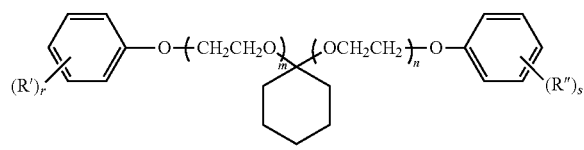

wherein R' and R" independently are an alkyl group having from 8 to about 20 carbon atoms;
m and n independently are an integer of from 1 to about 200; and
r and s independently are an integer of from 1 to 3.

2. The ketal of claim 1 wherein R' and R" independently are an alkyl group having from 8 to about 12 carbon atoms.

3. The ketal of claim 1 wherein R' and R" are the same alkyl group.

4. The ketal of claim 1 wherein R' and R" independently are a straight-chain alkyl group.

5. The ketal of claim 1 wherein R' and R" independently are a branched-chain alkyl group.

6. The ketal of claim 4 wherein R' and R" independently are a straight-chain alkyl group selected from 1-octyl; 2-octyl; 3-octyl; 4-octyl; 1-nonyl; 2-nonyl; 5-nonyl; 1-decyl; 2-decyl; 1-undecyl; 2-undecyl; 1-dodecyl; 2-dodecyl; 1-tridecyl; 1-tetradecyl; 2-tetradecyl; 1-pentadecyl; 1-hexadecyl; 2-hexadecyl; 1-heptadecyl; 1-octadecyl; 1-nonadecyl; and 1-eicosyl.

7. The ketal of claim 5 wherein R' and R" independently are a branched-chain alkyl group selected from 1,1,3,3-tetramethyl-1-butyl; 3-ethyl-2,2-dimethyl-3-pentyl; 2-propyl-1-pentyl; 1,1,4,4-tetramethyl-1-pentyl; 2,4,4-trimethyl-1-pentyl; 5,5-dimethyl-1-hexyl; 2-ethyl-1-hexyl; 3,5,5-trimethyl-1-hexyl; 2,6-dimethyl-4-heptyl; 3,6-dimethyl-3-heptyl; 4-methyl-3-heptyl; 6-methyl-2-heptyl; 2-butyl-i-octyl; 3,7-dimethyl-i-octyl; 3,7-dimethyl-3-octyl; 3-methyl-3-octyl; 2-hexyl-i-decyl; and 2-octyl-1-dodecyl.

8. The ketal of claim 5 wherein R' and R" independently are selected from 1,1,3,3-tetramethyl-1-butyl and 1,1,4,4-tetramethyl-1-pentyl.

9. The ketal of claim 1 wherein r and s are the same integer.

10. The ketal of claim 9 wherein r and s are 1.

11. The ketal of claim 10 wherein R' and R" are each attached at the 4 position of their respective phenyl group.

12. The ketal of claim 1 wherein m and n independently are an integer of from 1 to about 100.

13. The ketal of claim 1 wherein m and n independently are an integer of from 1 to about 30.

14. The ketal of claim 1 wherein m and n are the same integer.

15. The ketal of claim 1 which is at least partially water soluble and has a boiling point of about 200° C. or higher.

16. A method of preparing a ketal having the formula:

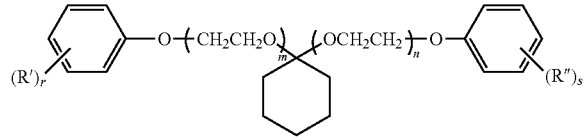

wherein R' and R" independently are an alkyl group having from 8 to about 20 carbon atoms; m and n independently are an integer of from 1 to about 200; and r and s independently are an integer of from 1 to 3; the method comprising reacting 1,1-dimethoxycyclohexane or 1,1-diethoxycyclohexane with an (alkylphenoxy)ethanol whose alkyl group has from 8 to about 20 carbon atoms, in the presence of an acid catalyst and an optional organic solvent at a temperature from about 60° C. to about 180° C., to produce a reaction mixture comprising a ketal and methanol or ethanol; then removing the produced methanol from 1,1-dimethoxycyclohexane or the produced ethanol from 1,1-diethoxycyclohexane to obtain a reaction mixture comprising a ketal depleted of methanol or ethanol; then optionally treating the reaction mixture comprising a ketal depleted of methanol or ethanol with an aqueous base until a pH of from about 6 to about 7 is attained, and then recovering the ketal by separating it from the produced aqueous phase.

17. The method of claim 16 wherein the optional organic solvent is present and is toluene.

18. The method of claim 16 wherein the optional organic solvent is present and is thereafter removed by evaporation.

19. The method of claim 16 wherein the acid catalyst is a Lowry-Bronsted acid.

20. The method of claim 19 wherein the Lowry-Bronsted acid is a sulfonic acid or phosphonic acid.

21. The method of claim 20 wherein the sulfonic acid is p-toluenesulfonic acid.

22. The method of claim 16 wherein the aqueous base is sodium hydroxide in water.

\* \* \* \* \*